(12) United States Patent
Betz et al.

(10) Patent No.: US 6,435,715 B1
(45) Date of Patent: Aug. 20, 2002

(54) RADIOGRAPHY DEVICE

(75) Inventors: Roland Betz, Viereth-Trunstadt; Peter Noegel, Effeltrich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/448,583

(22) Filed: Nov. 24, 1999

(30) Foreign Application Priority Data

Nov. 30, 1998 (DE) .......................................... 198 55 213

(51) Int. Cl.⁷ ................................................. G03B 5/00
(52) U.S. Cl. ........................................... 378/197; 378/4
(58) Field of Search ................................ 378/197, 196, 378/198, 4, 19

(56) References Cited

U.S. PATENT DOCUMENTS

| | | | | |
|---|---|---|---|---|
| 4,807,273 A | * | 2/1989 | Haendle | 378/197 |
| 4,894,855 A | | 1/1990 | Kresse | |
| 5,533,080 A | * | 7/1996 | Pelc | 378/5 |
| 6,125,163 A | * | 9/2000 | Barth et al. | 378/15 |
| 6,200,024 B1 | * | 3/2001 | Negrelli | 378/197 |

FOREIGN PATENT DOCUMENTS

| | | | | |
|---|---|---|---|---|
| DE | OS 196 11 705 | | 10/1997 | |
| EP | 0 917 855 A1 | * | 5/1999 | |
| JP | 40 6225867 A | * | 8/1994 | 378/4 |

* cited by examiner

*Primary Examiner*—David P. Porta
(74) *Attorney, Agent, or Firm*—Schiff Hardin & Waite

(57) ABSTRACT

A radiography device has an X-ray source and an X-ray reciever that are each arranged to be moved freely in space at a robot arm respective robots having a number of arms that can be displaced relative to one another by motor-drive. A central control unit controls the displacement of the robot arms of the two robots such that the X-ray source is always oriented to the X-ray receiver for producing an X-ray exposure.

4 Claims, 1 Drawing Sheet

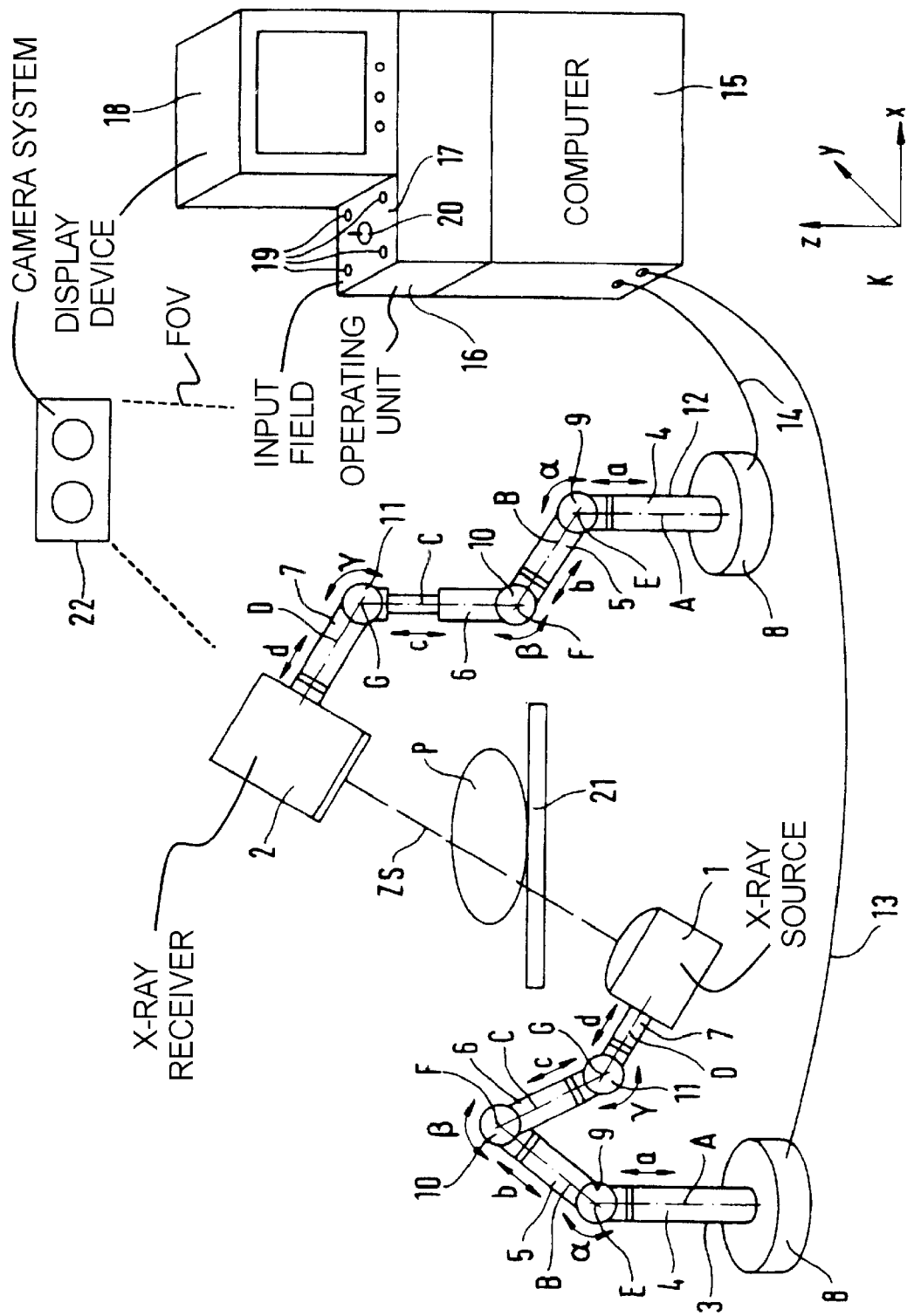

RADIOGRAPHY DEVICE

BACKGROUND OF THE INVENTION

1. Field of the Invention

The present invention relates to a radiography device having an X-ray source and an X-ray receiver.

2. Description of the Prior Art

Radiography devices are usually constructed such that the X-ray source and the X-ray receiver are fixedly arranged at a common mechanically rigid carrier, for instance a C-arm. The X-ray source and the X-ray receiver are arranged relative to one another at this carrier so that the center ray of an X-ray beam emanating from the X-ray source strikes on the detector surface of the X-ray receiver approximately in the middle thereof. The carrier typically can be moved relative to a subject that is being examined, the X-ray source and the X-ray receiver being constantly aligned relative to one another regardless of the displacements of the carrier.

A disadvantage of such rigid carriers is that they limit or obstruct the access to the patient in medical examinations.

German OS 196 11 705 teaches a radiography device with an X-ray source and an X-ray receiver, wherein the X-ray source and the X-ray receiver are respectively mounted at a stand such that they can be displaced three-dimensionally in space. In order to align the X-ray source and the X-ray receiver relative to one another such that the center ray of an X-ray beam emanating from the X-ray source strikes the detector surface of the X-ray receiver approximately in the middle thereof, detectors are provided in space that detect the positions of the X-ray receiver in space. Using the detected positions of the X-ray receiver, it is possible to adjust the X-ray source relative to the X-ray receiver such that the center ray of the X-ray beam emanating from the X-ray source strikes the detector surface of the X-ray receiver approximately in the middle thereof. The X-ray source thus always tracks the X-ray receiver.

The technical outlay required for the detection of the position of the X-ray receiver and for the tracking action of the X-ray source, which includes detectors that are arranged in space and a control means for the X-ray source and a control computer for the X-ray receiver, prove disadvantageous.

SUMMARY OF THE INVENTION

It is an object of the present invention to provide a radiography device wherein the X-ray source and the X-ray receiver are arranged such that they can be moved relative to one another freely, while always being aligned relative to one another, in a technically simple manner.

This object is inventively achieved in a radiography device having an X-ray source and an X-ray receiver which are each arranged so as to be moved freely in space at a robot arm of a robot having a number of arms that can be displaced relative to one another by motors, and having a central control unit which controls the displacement of the robot arms of the two robots such that the X-ray source is always oriented to the X-ray receiver for purposes of acquiring images. The X-ray source and the X-ray receiver are thus arranged at separate robot arms, respectively, so as to be freely displaceable in space. Because a mechanically rigid carrier that accepts both the X-ray source and the X-ray receiver is not used, in the case of medical radiological exams there results an improved access to a patient to be examined with the radiography device. Robots having a number of arms that can be displaced in a motor-driven manner relative to one another about axes, at which arms the X-ray source and the X-ray receiver respectively are arranged, offer a variety of adjustment possibilities for individual X-ray projections as well as multiple possibilities for movement sequences for capturing a series of radiographic images wherein the X-ray source and the X-ray receiver are displaced relative to an examination subject. The displacement of the robot arms of the two robots is controlled by the central control unit of the radiography device, so that the X-ray source and the X-ray receiver are always oriented to one another such that the center ray of an X-ray beam emanating from the X-ray source strikes the detector surface of the X-ray receiver approximately in the middle thereof in both individual X-ray projections (exposures) and in a series of X-ray projections (exposures).

In a version of the invention the robot arm at which the X-ray source is arranged and/or the robot arm at which the X-ray receiver is arranged have at least three degrees of freedom with respect to displacement of that robot arm. In this way, many adjustment possibilities of the X-ray source and the X-ray receiver are available merely by displacing the robot arm.

DESCRIPTION OF THE DRAWING

The single figure is a schematic illustration of a radiography device constructed and operating in accordance with the principles of the present invention.

DESCRIPTION OF THE PREFERRED EMBODIMENTS

The radiography device in the FIGURE has an X-ray source 1 and an X-ray receiver 2. The X-ray source 1 is arranged at a robot 3. In the exemplary embodiment, the robot 3 has a total of four arms 4 to 7 respectively having longitudinal axes A to D, which arms 4 to 7 can be displaced relative to one another by motor-drive. The robot arm 4 can be rotated around its axis A relative to a base 8 of the robot 3 and can be displaced along its axis A in the directions of the double arrow a. Similarly, the robot arms 5 to 7 can be rotated around their respective axes B to D and can be displaced along their respective axes B to D in the directions of the respective double arrows b to d. Additionally, the robot arm 5 can be rotated around an axis E of an axle 9; the robot arm 6 can be rotated around an axis F of an axle 10; and the robot arm 7 can be rotated around an axis G of an axle 11 (cf. double arrows α, β, γ). In this case, the axes E to G are perpendicular to the plane of the drawing. The displacement motors that effectuate the displacement motions of the robot arms 4 to 7 of the robot 3 are not explicitly illustrated in the FIGURE.

Thus the X-ray source 1 that is mounted at the end of the arm 7 of the robot 3 can be moved practically freely in space by virtue of the robot arms 4 to 7 that can be displaced relative to one another by motor-drive around the axes A to G and by virtue of the displacement of the arms 4 to 7 along the axes A to D.

In the exemplary embodiment, the X-ray receiver 2 is arranged at a robot 12, which is structurally and functionally identical to the robot 3. Since the robot 12 is structurally and functionally identical to the robot 3, its base, arms, axes, hinges and displacement possibilities are referenced with the same characters as for the robot 3. Analogously to the X-ray source 1, the X-ray receiver 2 is arranged at the end of the robot arm 7 of the robot 12. The displacement possibilities of a robot arm along its axis A to D are exemplarily illustrated for all robot arms 4 to 7 with reference to the arm 6 of the robot 12. In the case of the arm 6 of the robot 12, the displacement possibility of the arm 6 along its axis C is illustrated.

The robot 3 and the robot 12 are connected to a central control unit in the form of a computer 15 via respective cables 13 and 14. An operating unit 16 with an input (operating) field 17 and a display device 18 are also connected to the computer 15. The input field 17 includes operating buttons 19 and a joystick 20.

In the exemplary embodiment, a patient bed 21 and a patient P thereon are additionally schematically illustrated in the FIGURE.

To acquire an X-ray projection of a body region of a patient P, a treating physician can set the positions of the X-ray source 1 and the X-ray receiver 2 relative to the patient P for the desired X-ray projection from the operating unit 16 with the aid of the joystick 20. The displacement motions of the arms 4 to 7 of the robots 3 and 12 are controlled by the computer 15 according to the specifications of the physician; that is, the computer 15 computes the positions of the axes A to G of the robots 3 and 12 that correspond to the respectively desired positions of the X-ray source 1 and the X-ray receiver 2 and correspondingly controls the displacement motors of the axes A to G of the robots 3 and 12 directly or indirectly, for instance via a robot control that is provided in each of the two robots 3 and 12. The computer 15 ensures that the X-ray source 1 and the X-ray receiver 2 are always arranged relative to one another such that the center ray ZS of an X-ray beam emanating from the X-ray source 1 strikes the detector surface of the X-ray receiver 2 approximately in the middle thereof.

In a first operating mode of the radiography device, either the X-ray source 1 or the X-ray receiver 2 takes over a master function of sorts. That is, for instance, the displacement of the X-ray source 1 is controlled by the physician by means of the joystick 20, and the X-ray receiver 2, assuming a sort of slave function, is always oriented to the X-ray source 1 in real time. Since the position of the X-ray source 1 and that of the X-ray receiver 2 are always known to the computer 15 by means of the respective positions of the axes A to G, or the respective positions of the arms 4 to 7 of the robots 3 and 12, given a displacement of the X-ray source 1 by actuation of the joystick 20, the computer 15 can compute the corresponding position of the X-ray receiver 2 that is to be assumed and can cause it to assume the is position by a corresponding actuation of the displacement motors of the axes A to G of the robot 12 such that the X-ray source 1 and the X-ray receiver 2 are aligned relative to one another. It can be advantageous, if possible, to remove the input field 17 from the operating unit 16 so that the physician can control the displacement movement of the X-ray source 1 while standing immediately next to the patient. In this way, it is possible to adjust a precise setting of the X-ray source 1 and the X-ray receiver 2 in relation to the desired direction of projection of the radiogram.

In a second operating mode of the radiography device, the desired position of the X-ray source 1 or of the X-ray receiver 2 relative to a coordinate system K can be specified to the computer 15 by means of the operating button 19 or the joystick 20 of the input field 17, so that the computer 15 automatically causes displacement of the arms 4 to 7 of the robots 3 and 12 such that the X-ray source 1 and the X-ray receiver 2 assume the desired positions. The positions of the robots 3 and 12 in the coordinate system K are known to the computer 15, since they were imparted in an installation process, for example. Thus, based on the installation process the computer 15 knows the geometric locations of the robots 3 and 12 and the positions of the X-ray source 1 and the X-ray receiver 2 by means of the respective axis positions of the axes A to G of the arms 4 to 7 of the robots 3 and 12 relative to the coordinate system K.

The spatial correlation and the positions of the X-ray source 1 and the X-ray receiver 2 can be displayed on the display device 18.

A camera system 22 can be arranged in the room and has a field of view FOV that encompasses at least the patient bed 21 and the patient P thereon, and is connected to the computer 15. By means of this camera system 22, it is also possible to determine the positions of the patient P and of the patient bed 21 in the coordinate system K by suitable methods of image analysis. In this way, the patient bed 21 and the patient P and their relative positions to the X-ray source 1 and the X-ray receiver 2 can be displayed on the display device 18, so that orienting the X-ray source 1 and the X-ray receiver 2 relative to a body region of the patient P is easier for the physician.

The robots that are illustrated in the exemplary embodiment are merely examples and can deviate from the given embodiment with respect to the arrangement of their axes and the number of arms, as well as with respect to the motion possibilities of the arms.

The components required to drive the X-ray source 1 and the X-ray receiver 2 and the connection of these components are not explicitly illustrated in the FIGURE, since they are realized in a manner that is known.

In the exemplary embodiment, the robots 3 and 12 are arranged with their respective bases 8 on the floor of a treatment room, but the robots can alternatively be secured on the wall or the ceiling of the treatment room.

Besides this, the robots can be constructed such that they can be lowered into the floor.

As already indicated, it is possible to generate either single radiograms or a series of radiograms with the inventive radiography device. In the latter case, the X-ray source 1 and the X-ray receiver 2 are displaced by means of the robot arms 4 to 7 through an angle range of approximately 1800 around the body region of the patient P that is to be examined and displayed, whereby the computer 15 controls the displacement of the robot arms 4 to 7 such that the X-ray source 1 and the X-ray receiver 2 are always aligned relative to one another; that is, the center ray ZS always strikes the detector surface of the X-ray receiver 2 approximately in the middle thereof. During the displacement motion of the X-ray source 1 and the X-ray receiver 2, approximately 100 to 500 radiograms of the body region of the patient P are picked up from different projection angles. The thus acquired radiograms can then be used to reconstruct 3D images of the body region of the patient P.

The inventive device has been described in the case of a medical examination, but is not limited to medical uses.

Although modifications and changes may be suggested by those skilled in the art, it is the intention of the inventors to embody within the patent warranted hereon all changes and modifications as reasonably and properly come within the scope of their contribution to the art.

We claim:

1. A radiography device comprising:
    an X-ray source;
    an X-ray receiver;
    a first robot having a connected plurality of first robot arms, including one of said first robot arms at which said X-ray source is mounted, all of said first robot arms being freely displaceable in space by motor drive;

a second robot having a connected plurality of second robot arms, including one of said second robot arms at which said X-ray receiver is mounted, all of said second robot arms being freely displaceable in space by motor drive;

a central control unit electronically connected to said first robot and to said second robot for controlling displacement of said plurality of first robot arms and said plurality of second robot arms for orienting said X-ray source and said X-ray receiver at a plurality of respective positions in spaces while always maintaining said X-ray source and said X-ray receiver in relative positions relative to each other for allowing a radiographic image of a subject to be acquired, to acquire a plurality of radiographic images of the subject; and a computer supplied with said plurality of radiographic images for generating a three-dimensional image of said subject from said plurality of radiographic images.

2. A radiography device as claimed in claim 1 wherein said one of said first robot arms at which said X-ray source is mounted is displaceable with at least three degrees of freedom.

3. A radiography device as claimed in claim 1 wherein said one of said second robot arms at which said X-ray receiver is mounted is displaceable with at least three degrees of freedom.

4. A radiography device as claimed in claim 1 wherein said one of said robot arms at which said X-ray source is mounted is displaceable with at least three degrees of freedom, and wherein said one of said second robot arms at which said X-ray receiver is mounted is displaceable with at least three degrees of freedom.

* * * * *